United States Patent
Fang et al.

(10) Patent No.: US 11,827,589 B2
(45) Date of Patent: Nov. 28, 2023

(54) METHODS FOR ISOBUTYLENE CONVERSION TO C5+ COMPOUNDS

(71) Applicant: Lyondell Chemical Technology, L.P., Houston, TX (US)

(72) Inventors: Linn Fang, Houston, TX (US); Daniel F. White, Houston, TX (US); Lei Zhang, League City, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 17/951,578

(22) Filed: Sep. 23, 2022

(65) Prior Publication Data

US 2023/0107520 A1  Apr. 6, 2023

Related U.S. Application Data

(60) Provisional application No. 63/251,903, filed on Oct. 4, 2021.

(51) Int. Cl.
  *C07C 6/04* (2006.01)
  *C07C 5/27* (2006.01)
  *C10L 1/06* (2006.01)

(52) U.S. Cl.
  CPC .............. *C07C 5/2708* (2013.01); *C07C 6/04* (2013.01); *C10L 1/06* (2013.01); *C10L 2200/0423* (2013.01); *C10L 2270/023* (2013.01); *C10L 2290/24* (2013.01)

(58) Field of Classification Search
  CPC . C07C 5/2708; C07C 6/04; C10L 1/06; C10L 2200/0423; C10L 2270/023; C10L 2290/24

USPC ........................................................ 585/324
See application file for complete search history.

(56) References Cited

U.S. PATENT DOCUMENTS

| | | | |
|---|---|---|---|
| 2,882,243 | A | 4/1959 | Milton |
| 2,882,244 | A | 4/1959 | Milton |
| 3,130,007 | A | 4/1964 | Breck |
| 3,526,676 | A | 9/1970 | Howman et al. |
| 3,702,886 | A | 11/1972 | Argauer |
| 3,709,979 | A | 1/1973 | Chu |
| 3,832,449 | A | 8/1974 | Rosinski |
| 3,933,974 | A | 1/1976 | Winquist |
| 4,000,248 | A | 12/1976 | Martin |

(Continued)

FOREIGN PATENT DOCUMENTS

| | | |
|---|---|---|
| EP | 111808 A2 | 6/1984 |
| EP | 159624 A2 | 10/1985 |

OTHER PUBLICATIONS

Flanigen et al., Aluminophosphate Molecular Sieves and the Periodic Table, Pure & Appl. Chem., vol. 58, No. 10, pp. 1351-1358, 1986.

(Continued)

*Primary Examiner* — Prem C Singh
*Assistant Examiner* — Francis C Campanell

(57) ABSTRACT

Methods of converting isobutylene to C5+ compounds. The methods may include contacting isobutylene with a skeletal isomerization catalyst to provide a mixture of $C_4$ olefins, and then contacting the mixture of $C_4$ olefins with a metathesis catalyst to convert the mixture of $C_4$ olefins to a product mixture. The product mixture may include $C_{5+}$ olefins.

19 Claims, 4 Drawing Sheets

(56) References Cited

U.S. PATENT DOCUMENTS

| | | | |
|---|---|---|---|
| 4,016,245 | A | 4/1977 | Plank |
| 4,060,590 | A | 11/1977 | Whittam |
| 4,076,842 | A | 2/1978 | Plank |
| 4,375,573 | A | 3/1983 | Young |
| 4,440,871 | A | 4/1984 | Lok |
| 4,500,651 | A | 2/1985 | Lok |
| 4,544,143 | A | 10/1985 | Cooper |
| 4,567,029 | A | 1/1986 | Wilson |
| 4,942,007 | A | 7/1990 | Kunimoto |
| 8,395,005 | B2 | 3/2013 | Coleman |
| 2004/0192994 | A1* | 9/2004 | Bridges ................ C07C 5/2556 585/664 |
| 2005/0250969 | A1 | 11/2005 | Bridges |
| 2013/0245348 | A1 | 9/2013 | Vermeiren et al. |

OTHER PUBLICATIONS

International Search Report dated Apr. 26, 2023 for EP Patent Application 22198202.8.

* cited by examiner

METHODS FOR ISOBUTYLENE CONVERSION TO C5+ COMPOUNDS

CROSS-REFERENCE TO RELATED APPLICATIONS

This application claims the benefit of priority to U.S. Provisional Patent Application No. 63/251,903, filed on Oct. 4, 2021, which is incorporated herein by reference in its entirety.

FIELD OF THE DISCLOSURE

This disclosure relates to the production of C5+ compounds. More specifically, this disclosure relates to the production of C5+ compounds by the conversion of isobutylene.

BACKGROUND OF THE DISCLOSURE

In many instances, it is desirable to convert an alkene, such as normal butene, to a methyl branched alkene, for example isobutylene, by mechanisms such as structural isomerization. Such converted isoalkenes then can be reacted further, such as by polymerization or oxidation, to form useful products. Isobutylene, for example, has been used as a major feedstock for oxygenate fuels, such as methyl tert-butyl ether (MTBE) and ethyl tertiary butyl ether (ETBE).

Normal alkenes containing four carbon atoms (1-butene, trans-2-butene and cis-2-butene) and five carbon atoms (1-pentene, trans-2-pentene, and cis-2-pentene) are relatively inexpensive starting compounds. Conventionally, butenes and amylenes, including to a minor extent isobutylene and isoamylene, are obtained as a by-product from refinery and petrochemical processes such as catalytic and thermal cracking units.

Olefins such as n-butylenes can be converted to branched olefin species, such as isobutylene, by skeletal isomerization over zeolite-based catalysts. The zeolite-based catalysts may have sufficient acidity to catalyze the skeletal isomerization of olefins. Zeolite materials, both natural and synthetic, are known to have catalytic properties for many hydrocarbon processes. Zeolites typically are ordered porous crystalline aluminosilicates having a definite structure with cavities interconnected by channels. The cavities and channels throughout the crystalline material generally can be of such a size to allow selective separation of hydrocarbons.

There remains a need for methods for converting isobutylene into one or more products, including economically valuable products, such as gasoline.

SUMMARY OF THE DISCLOSURE

Provided herein are processes for converting isobutylene, including processes that convert isobutylene to a gasoline blend, along with a propylene product via a tandem catalysis of skeletal isomerization and metathesis. In some embodiments, isobutylene is subjected to tandem catalysis to produce a gasoline blend product along with propylene as a major byproduct.

Methods of converting isobutylene are provided. In some embodiments, the methods include contacting isobutylene and a skeletal isomerization catalyst to convert the isobutylene to a mixture of $C_4$ olefins; and contacting the mixture of $C_4$ olefins with a metathesis catalyst to convert the mixture of $C_4$ olefins to a product mixture.

In some embodiments, the mixture of $C_4$ olefins includes butene-1, cis-butene-2, trans-butene-2, unreacted isobutylene, or a combination thereof. In some embodiments, the product mixture includes ethylene, propylene, unreacted isobutylene, butene-1, cis-butene-2, trans-butene-2, and $C_{5+}$ olefins. In some embodiments, the $C_{5+}$ olefins are present in the product mixture at an amount of at least 25%, by weight, based on the weight of the product mixture.

Additional aspects will be set forth in part in the description which follows, and in part will be obvious from the description, or may be learned by practice of the aspects described herein. The advantages described herein may be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

Certain embodiments of the disclosure will hereafter be described with reference to the accompanying drawings, wherein like reference numerals denote like elements. It should be understood, however, that the accompanying figures illustrate the various implementations described herein and are not meant to limit the scope of various technologies described herein, and.

DETAILED DESCRIPTION OF THE DISCLOSURE

Figure 1:
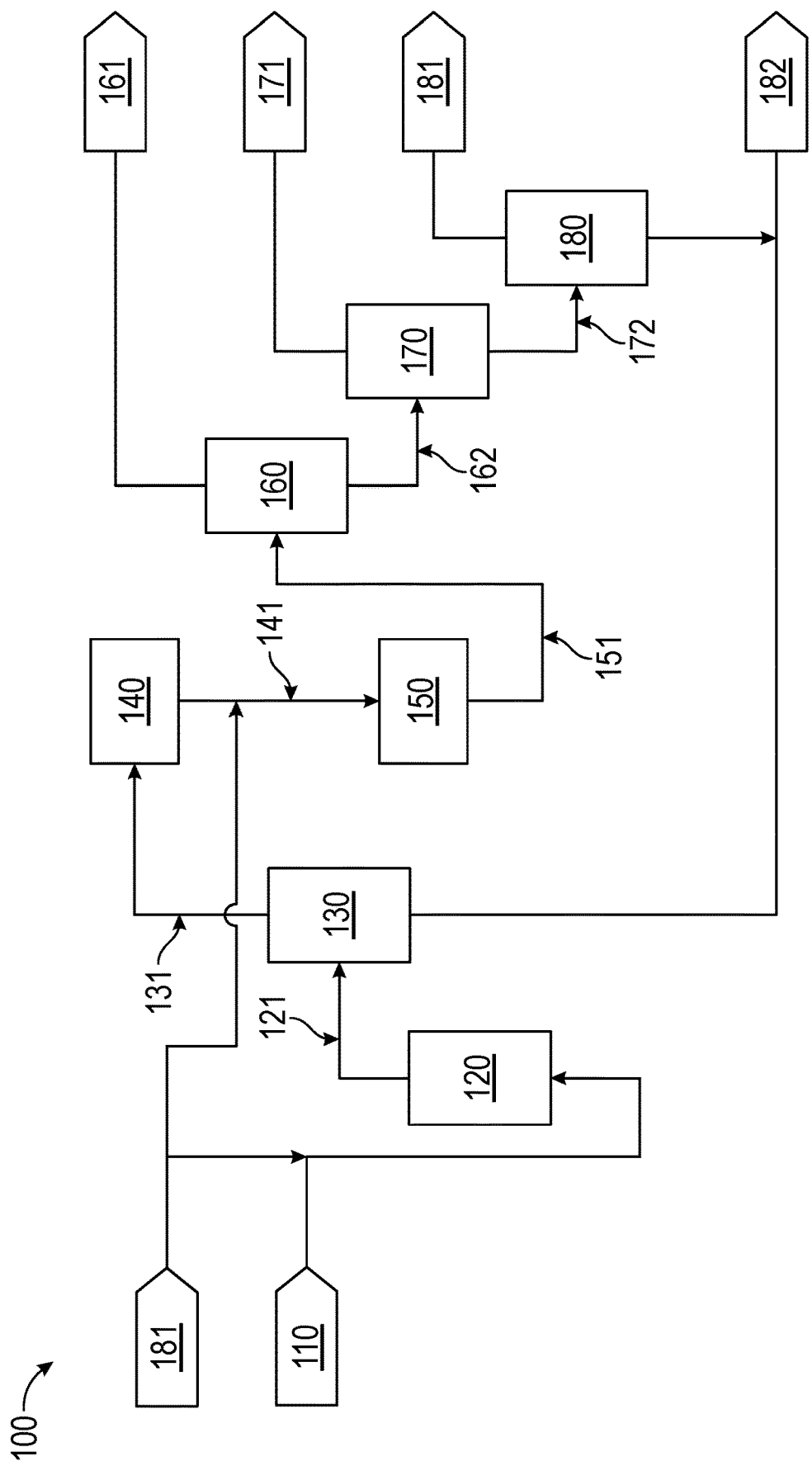
FIG. 1 depicts a schematic of an embodiment of a method described herein.

In the following description, numerous details are set forth to provide an understanding of some embodiments of the present disclosure. However, it will be understood by those of ordinary skill in the art that the system and/or methodology may be practiced without these details and that numerous variations or modifications from the described embodiments are possible. This description is not to be taken in a limiting sense, but rather made merely for the purpose of describing general principles of the implementations. The scope of the described implementations should be ascertained with reference to the issued claims.

Provided herein are methods for converting isobutylene. In some embodiments, the methods include contacting isobutylene and a skeletal isomerization catalyst to convert the isobutylene to a mixture of $C_4$ olefins.

As used herein, the phrase "$C_2$ olefins", "$C_3$ olefins", "$C_4$ olefins", "$C_{5+}$ olefins", and the like refer to olefins (i.e., alkenes) that include 2, 3, 4, or 5 or more carbon atoms, respectively.

The isobutylene may be a feed consisting of isobutylene, or a feed that includes isobutylene and one or more other components, such as $C_2$ olefins, $C_3$ olefins, or a combination thereof. The isobutylene may be a feed that includes isobutylene and butenes recycled from embodiments of the methods described herein (see, e.g., the recycled butenes 181, 281 of FIG. 1 and FIG. 2, respectively). The isobutylene may be a feed that includes isobutylene and (i) one or more other components, such as $C_2$ olefins, $C_3$ olefins, or a combination thereof, (ii) butenes recycled from embodiments of the methods described herein, or (iii) a combination thereof.

In some embodiments, the catalyst includes a zeolitic catalyst, which may contain a zeolite from the ferrierite group (FER structure).

Generally, the term "zeolite" includes a wide variety of both natural and synthetic positive ion-containing crystalline aluminosilicate materials, including molecular sieves. They generally are characterized as crystalline aluminosilicates which include networks of $SiO_4$ and $AlO_4$ tetrahedra in which silicon and aluminum atoms are cross-linked in a three-dimensional framework by sharing of oxygen atoms. This framework structure contains channels or interconnected voids that are occupied by cations, such as sodium, potassium, ammonium, hydrogen, magnesium, calcium, and water molecules. The water may be removed reversibly, such as by heating, which leaves a crystalline host structure available for catalytic activity. The term "zeolite" in this specification is not limited to crystalline aluminosilicates. The term as used herein also includes silicoaluminophosphates (SAPO), metal integrated aluminophosphates (MeAPO and ELAPO), metal integrated silicoaluminophosphates (MeAPSO and ELAPSO). The MeAPO, MeAPSO, ELAPO, and ELAPSO families have additional elements included in their framework. For example, Me represents the elements Co, Fe, Mg, Mn, or Zn, and El represents the elements Li, Be, Ga, Ge, As, or Ti. An alternative definition would be "zeolitic type molecular sieve" to encompass the materials useful for this disclosure.

Developments in the art have resulted in formation of many synthetic zeolitic crystalline materials. Crystalline aluminosilicates are the most prevalent and, as described in the patent literature and in the published journals, are designated by letters or other convenient symbols. Zeolites have been specifically named and described as Zeolite A (U.S. Pat. No. 2,882,243), Zeolite X (U.S. Pat. No. 2,882,244), Zeolite Y (U.S. Pat. No. 3,130,007), Zeolite ZSM-5 (U.S. Pat. No. 3,702,886), Zeolite ZSM-11 (U.S. Pat. No. 3,709,979), Zeolite ZSM-12 (U.S. Pat. No. 3,832,449), Zeolite ZSM-23 (U.S. Pat. No. 4,076,842), Zeolite ZSM-35 (U.S. Pat. No. 4,016,245), Zeolite ZSM-48 (U.S. Pat. No. 4,375,573), Zeolite NU-1 (U.S. Pat. No. 4,060,590) and others. Various ferrierite zeolites, including the hydrogen form of ferrierite, are described in U.S. Pat. Nos. 3,933,974, 4,000,248 and 4,942,007 and patents cited therein. SAPO-type catalysts are described in U.S. Pat. No. 4,440,871. MeAPO type catalysts are described in U.S. Pat. Nos. 4,544,143 and 4,567,029; ELAPO catalysts are described in U.S. Pat. No. 4,500,651, and ELAPSO catalysts are described in European Patent Application 159,624.

EP-A-0 111 808 discloses an isomerization catalyst formed from a zeolite of the pentasil family such as ZSM-12 and a kaolinite-containing clay mineral.

In some embodiments, the zeolite catalyst useful in the processes of the methods herein includes a zeolite having a one-dimensional pore structure with a pore size ranging from greater than 0.42 nm and less than 0.7 nm. The zeolite catalyst, in some embodiments, includes substantially only zeolites with the specified pore size in one dimension. Zeolites having pore sizes greater than 0.7 nm, in some instances, may be susceptible to unwanted aromatization, oligimerization, alkylation, coking and by-product formation. Further, two or three-dimensional zeolites having a pore size greater than 0.42 nm in two or more dimensions may permit dimerization and trimerization of the alkene.

In some embodiments, zeolites used in the processes of this disclosure are the hydrogen form of ferrierite and isotypic structures thereof, such as FU-9, NU-23 and ZSM-35. The isotypic structures of these frameworks, known under other names, are considered to be equivalent. An overview describing the framework compositions of many of these zeolites is provided in New Developments in Zeolite Science Technology, "Aluminophosphate Molecular Sieves and the Periodic Table," Hanigen et al. (Kodansha Ltd., Tokyo, Japan 1986).

The mixture of $C_4$ olefins may include two or more different $C_4$ olefins, and one or more non-$C_4$ olefins, such as $C_2$ olefins, $C_3$ olefins, and/or $C_{5+}$ olefins. In some embodiments, the mixture of $C_4$ olefins includes butene-1, cis-butene-2, trans-butene-2, unreacted isobutylene, or a combination thereof. In some embodiments, the mixture of $C_4$ olefins includes butene-1, cis-butene-2, trans-butene-2, and unreacted isobutylene.

In some embodiments, isobutylene and a skeletal isomerization catalyst are contacted for a time effective to achieve a thermodynamic equilibrium at a temperature and a pressure. The temperature may be about 500° F. (about 260° C.) to about 1,150° F. (about 621° C.), about 500° F. (about 260° C.) to about 900° F. (about 482° C.), about 600° F. (about 315° C.) to about 800° F. (about 427° C.), about 700° F. (about 371° C.) to about 800° F. (about 427° C.), about 750° F. (about 399° C.) to about 800° F. (about 427° C.), or about 750° F. (about 399° C.). The pressure may be 0.5 bar or greater, or, in some instances, less than 0.5 bar. In some embodiments, the pressure may be in the range of from about 0.5 barg to about 10 barg. In some embodiments, the pressure may be in the range of from about 1 barg to about 5 barg. In some embodiments, the pressure may be in the range of from about 0.10 barg to about 2 barg. In some embodiments, the pressure may be in the range of from about 1.0 barg to about 2.5 barg. In some embodiments, the pressure may be in the range of from about 0.25 barg to about 1.0 barg.

In some embodiments, butene-1, at thermodynamic equilibrium, is present in the mixture of $C_4$ olefins at an amount of about 5% to about 25%, by weight, based on the weight of the $C_4$ olefins. In some embodiments, butene-1, at thermodynamic equilibrium, is present in the mixture of $C_4$ olefins at an amount of about 5% to about 20%, by weight, based on the weight of the $C_4$ olefins. In some embodiments, butene-1, at thermodynamic equilibrium, is present in the mixture of $C_4$ olefins at an amount of about 10% to about 20%, by weight, based on the weight of the $C_4$ olefins. In some embodiments, butene-1, at thermodynamic equilibrium, is present in the mixture of $C_4$ olefins at an amount of about 10% to about 15%, by weight, based on the weight of the $C_4$ olefins. In some embodiments, butene-1, at thermodynamic equilibrium, is present in the mixture of $C_4$ olefins at an amount of about 12%, by weight, based on the weight of the $C_4$ olefins.

In some embodiments, cis-butene-2 and trans-butene-2, at thermodynamic equilibrium, are present in the mixture of $C_4$ olefins at a total amount of about 20% to about 50%, by weight, based on the weight of the $C_4$ olefins. When used to describe a concentration of cis-butene-2 and trans-butene-2, the phrase "total amount" refers to the sum of the concentrations of cis-butene-2 and trans-butene-2; for example, if cis-butene-2 and trans-butene-2 are present at concentrations of 10% and 15%, by weight, respectively, then the cis-butene-2 and trans-butene-2 are present at a "total amount" of about 25%, by weight. In some embodiments, cis-butene-2 and trans-butene-2, at thermodynamic equilibrium, are present in the mixture of $C_4$ olefins at a total amount of about 25% to about 45%, by weight, based on the weight of the $C_4$ olefins. In some embodiments, cis-butene-2 and trans-butene-2, at thermodynamic equilibrium, are present in the mixture of $C_4$ olefins at a total amount of about 30% to about 40%, by weight, based on the weight of the $C_4$ olefins. In some embodiments, cis-butene-2 and trans-butene-2, at thermodynamic equilibrium, are present in the mixture of $C_4$ olefins at a total amount of about 35% to about 40%, by weight, based on the weight of the $C_4$ olefins. In some embodiments, cis-butene-2 and trans-butene-2, at thermodynamic equilibrium, are present in the mixture of $C_4$ olefins at a total amount of about 36%, by weight, based on the weight of the $C_4$ olefins.

In some embodiments, at thermodynamic equilibrium, the mixture of $C_4$ olefins includes ethylene, propylene, $C_{5+}$ olefins, or a combination thereof, and the ethylene, propylene, $C_{5+}$ olefins, or a combination thereof are present in the mixture of $C_4$ olefins at a total amount of 0% to about 15%, by weight, based on the weight of the mixture of $C_4$ olefins. When used to describe a concentration of ethylene, propylene, $C_{5+}$ olefins, or a combination thereof, the phrase "total amount" refers to the sum of the concentrations of ethylene, propylene, and $C_{5+}$ olefins; for example, if ethylene, propylene, and $C_{5+}$ olefins are present at concentrations of 2%, 3%, and 5%, by weight, respectively, then the ethylene, propylene, and $C_{5+}$ olefins are present at a "total amount" of about 10%, by weight. In some embodiments, at thermodynamic equilibrium, the mixture of $C_4$ olefins includes ethylene, propylene, $C_{5+}$ olefins, or a combination thereof, and the ethylene, propylene, $C_{5+}$ olefins, or a combination thereof are present in the mixture of $C_4$ olefins at a total amount of about 5% to about 15%, by weight, based on the weight of the mixture of $C_4$ olefins. In some embodiments, at thermodynamic equilibrium, the mixture of $C_4$ olefins includes ethylene, propylene, $C_{5+}$ olefins, or a combination thereof, and the ethylene, propylene, $C_{5+}$ olefins, or a combination thereof are present in the mixture of $C_4$ olefins at a total amount of about 8% to about 12%, by weight, based on the weight of the mixture of $C_4$ olefins. In some embodiments, at thermodynamic equilibrium, the mixture of $C_4$ olefins includes ethylene, propylene, $C_{5+}$ olefins, or a combination thereof, and the ethylene, propylene, $C_{5+}$ olefins, or a combination thereof are present in the mixture of $C_4$ olefins at a total amount of about 10%, by weight, based on the weight of the mixture of $C_4$ olefins.

When a mixture of $C_4$ olefins includes ethylene, propylene, $C_{5+}$ olefins, or a combination thereof, then the methods may include separating the ethylene, the propylene, the $C_{5+}$ olefins, or a combination thereof from the mixture of $C_4$ olefins prior to the contacting of the mixture of $C_4$ olefins with a metathesis catalyst as described herein. The separating of the ethylene, the propylene, and/or the $C_{5+}$ olefins may remove all or a portion of each component.

When a mixture of $C_4$ olefins includes $C_{5+}$ olefins, the methods, in some embodiments, include separating the $C_{5+}$ olefins from the mixture of $C_4$ olefins prior to the contacting of the mixture of $C_4$ olefins with a metathesis catalyst as described herein. The $C_{5+}$ olefins then may be subjected to further processing known in the art. In some embodiments, the methods described herein include (i) blending the $C_{5+}$ olefins with one or more other components to produce a product, (ii) processing the $C_{5+}$ olefins in a hydrotreater, or (iii) a combination thereof. The product may include gasoline.

In some embodiments, the methods described herein include contacting a mixture of $C_4$ olefins with a metathesis catalyst to convert the mixture of $C_4$ olefins to a product mixture.

Generally, any catalyst capable of facilitating metathesis may be used as the metathesis catalyst. The metathesis catalyst may be used in the presence of an isomerization catalyst. The isomerization catalyst may be the same catalyst or a different catalyst than the skeletal isomerization catalyst used to contact isobutylene. In some embodiments, the metathesis catalyst includes tungsten, molybdenum, or rhenium. In some embodiments, the metathesis catalyst is used in the presence of an isomerization catalyst selected from MgO or $Al_2O_3$ supported $K_2O$.

U.S. Pat. No. 8,395,005, which is incorporated herein by reference, discloses examples of metathesis catalysts. In some embodiments, a metathesis catalyst includes a transition metal oxide. The transition metal oxide may include a transition metal selected from Group VIB to Group VIIIB of the periodic table. In some embodiments, the transition metal oxide includes W, Mo, Re, Ru, or a combination thereof. The metathesis catalyst may be a homogeneous organometallic catalyst. The metathesis catalyst may be a solid supported catalyst. The metathesis catalyst may be in the form of a powder or particulates. Suitable catalyst forms may include includes beads, granules, pellets, extrudates, tablets, agglomerates, honeycomb monolith, and the like, generally having a particle size of greater than 1 mm. A metathesis catalyst also may be used in combination with an isomerization catalyst, a metathesis catalyst promoter, or a combination thereof.

In some embodiments, the metathesis catalyst includes tungsten oxide supported on a silica carrier. Examples of silica carriers include high purity silicas, i.e., those having a very low level of sodium (e.g., less than 2000 ppm Na2O) and aluminum (e.g., less than 2000 ppm $Al_2O_3$). Generally, the silica carrier may have a surface area of at least 10 square meters per gram. In some embodiments, the surface area is at least 50 square meters per gram. To prepare a tungsten oxide-on-silica catalyst, an aqueous solution or suspension of tungsten oxide or a tungsten oxide precursor may be used to contact a silica carrier. Suitable tungsten oxide precursors include compounds that are convertible to the oxide form under calcination conditions, such as, for example, halides, sulfides, sulfates, nitrates, carboxylates, and the like, and mixtures thereof. Exemplary tungsten compounds may include tungsten pentabromide, tungsten dichloride, tungsten tetrachloride, tungsten hexafluoride, tungsten trioxide, tungsten dioxydichloride, tungsten trisulfide, metatungstic acid, orthotungstic acid, ammonium phosphotungstate, ammonium metatungstate, and mixtures thereof. The tungsten oxide-on-silica catalyst, in some embodiments, is used in a fixed-bed reactor.

The contacting of the mixture of $C_4$ olefins and the metathesis catalyst may occur at any temperature and pressure effective to produce a desired product. The pressure, in some embodiments, is ambient pressure to about 30 barg. In some embodiments, the pressure may be in the range of from about 1.0 barg to about 25 barg. In some embodiments, the pressure may be in the range of from about 1.0 barg to about 6 barg. In some embodiments, the pressure may be in the range of from about 4.0 barg to about 10 barg. In some embodiments, the pressure may be in the range of from about 8.0 barg to about 20 barg. In some embodiments, the pressure may be in the range of from about 12.0 barg to about 16 barg. In some embodiments, the pressure may be in the range of from about 8.0 barg to about 14 barg. In some embodiments, the metathesis catalyst includes tungsten, and the contacting of the mixture of $C_4$ olefins and the metathesis catalyst occurs at a temperature of about 200° C. to about 400° C. In some embodiments, the metathesis catalyst includes molybdenum, and the contacting of the mixture of $C_4$ olefins and the metathesis catalyst occurs at a temperature of about 70° C. to about 200° C. In some embodiments, the metathesis catalyst includes rhenium, and the contacting of the mixture of $C_4$ olefins and the metathesis catalyst occurs at a temperature of about 20° C. to about 100° C.

The product mixture may include ethylene, propylene, unreacted isobutylene, butene-1, cis-butene-2, trans-butene-2, $C_{5+}$ olefins, or a combination thereof. In some embodiments, the product mixture includes ethylene, propylene, unreacted isobutylene, butene-1, cis-butene-2, trans-butene-2, and $C_{5+}$ olefins.

In some embodiments, the $C_{5+}$ olefins are present in the product mixture at an amount of at least 25%, by weight, based on the weight of the product mixture. In some embodiments, the $C_{5+}$ olefins are present in the product mixture at an amount of at least 30%, by weight, based on the weight of the product mixture. In some embodiments, the $C_{5+}$ olefins are present in the product mixture at an amount of at least 35%, by weight, based on the weight of the product mixture.

In some embodiments, the methods include separating the $C_{5+}$ olefins from the product mixture. The $C_{5+}$ olefins then may be subjected to further processing known in the art. In some embodiments, the methods described herein include (i) blending the $C_{5+}$ olefins with one or more other components to produce a product, (ii) processing the $C_{5+}$ olefins in a hydrotreater, or (iii) a combination thereof. The product may include gasoline. The $C_{5+}$ olefins obtained from the product mixture may be combined with the $C_{5+}$ olefins obtained from the mixture of $C_4$ olefins (see, e.g., FIG. 1 and FIG. 2). The combined $C_{5+}$ olefins then may be subjected to further processing as described herein.

In some embodiments, the methods include separating ethylene from the product mixture to create a substantially ethylene-free product mixture. As used herein, the phrase "substantially ethylene-free product mixture" refers to a mixture that includes no more than 1% or 0.1%, by weight, of ethylene. In some embodiments, the methods include separating the propylene from the substantially ethylene-free product mixture to produce a substantially ethylene- and propylene-free product mixture. As used herein, the phase "substantially propylene-free product mixture" refers to a mixture that includes no more than 1% or 0.1%, by weight, of propylene. In some embodiments, the methods include separating the unreacted isobutylene, the butene-1, the cis-butene-2, and the trans-butene-2 from the substantially ethylene- and propylene-free product mixture to produce a substantially ethylene-, propylene-, and butene-free product mixture including the $C_{5+}$ olefins. As used herein, the phase "substantially butene-free product mixture" refers to a mixture that includes no more than 1% or 0.1%, by weight, of butenes.

In some embodiments, an amount of the unreacted isobutylene that is present in the mixture of $C_4$ olefins is about 1.5 times to about 2.5 times greater than an amount of the unreacted isobutylene that is present in the product mixture. In some embodiments, an amount of the unreacted isobutylene that is present in the mixture of $C_4$ olefins is about 2 times greater than an amount of the unreacted isobutylene that is present in the product mixture.

A schematic of an embodiment of a method described herein is depicted at FIG. 1. The method 100 of FIG. 1 includes a feed of isobutylene 110 that is provided to an isomerization reactor 120. The isobutylene 110 is contacted with a skeletal isomerization catalyst in the isomerization reactor 120 to produce a mixture of $C_4$ olefins 121. The mixture of $C_4$ olefins 121 may also include ethylene, propylene, and $C_{5+}$ olefins.

Thereafter, the mixture of $C_4$ olefins 121 is provided to an apparatus 130 configured to separate the mixture of $C_4$ olefins 121 into a stream including the $C_4$ olefins 131 and a stream including the $C_{5+}$ olefins 182.

The stream including $C_4$ olefins 131 is then treated with an apparatus 140 configured to remove any $C_4$ alcohols. The resulting stream of $C_4$ olefins 141 is then provided to a metathesis reactor 150. In the metathesis reactor 150, the stream of $C_4$ olefins 141 is contacted with a metathesis catalyst, optionally in the presence of an isomerization catalyst, to produce a product mixture 151 that may include ethylene, propylene, unreacted isobutylene, butene-1, cis-butene-2, trans-butene-2, and $C_{5+}$ olefins.

The product mixture then is provided to an apparatus 160 configured to separate a stream including ethylene 161 from the ethylene-free product mixture 162.

The ethylene-free product mixture 162 then is provided to an apparatus 170 configured to separate a stream including propylene 171 from the ethylene- and propylene-free product mixture 172.

The ethylene- and propylene-free product mixture 172 then is provided to an apparatus 180 configured to separate a stream including butenes 181 from a stream including $C_{5+}$ olefins 182. The stream including butenes 181 may optionally be recycled, as depicted at FIG. 1. The stream including butenes 181 may be combined with the feed of isobutylene, combined with the stream of $C_4$ olefins 141, provided directly to apparatus 150 (not shown), or a combination thereof.

The stream of $C_{5+}$ olefins of apparatus 130 and apparatus 180 may be combined as depicted at FIG. 1, or the streams may be handled or treated separately. The method schematically depicted at FIG. 1 may be aided by one or more other components known to those of ordinary skill in the art, such as one or more valves, furnaces, compressors, pumps, etc.

Figure 2:
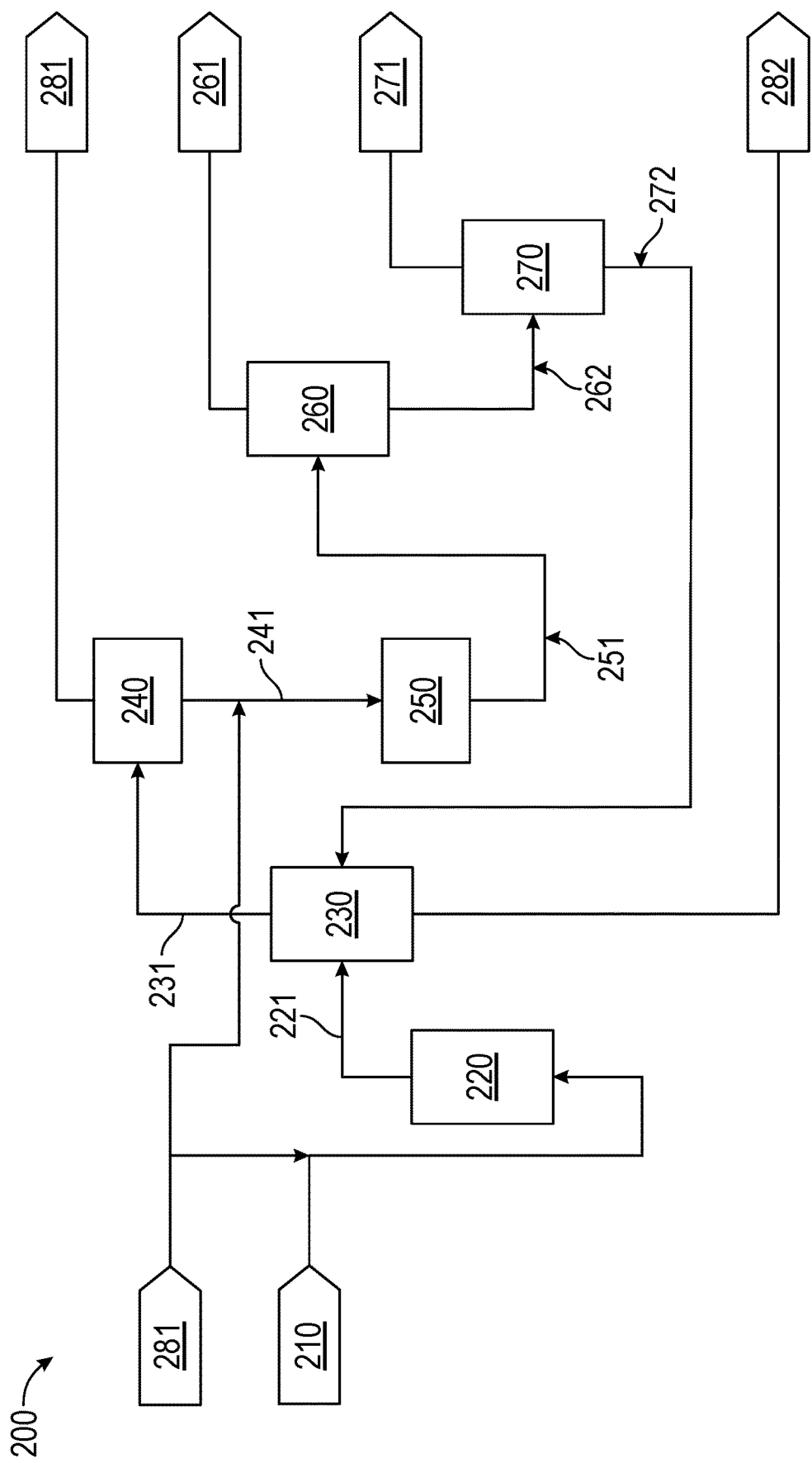
FIG. 2 depicts a schematic of an embodiment of a method described herein.

A schematic of an embodiment of a method described herein is depicted at FIG. 2. The method 200 of FIG. 2 includes a feed of isobutylene 210 that is provided to an isomerization reactor 220. The isobutylene 210 is contacted with a skeletal isomerization catalyst in the isomerization reactor 220 to produce a mixture of $C_4$ olefins 221. The mixture of $C_4$ olefins 221 may also include ethylene, propylene, and $C_{5+}$ olefins.

Therefore, the mixture of $C_4$ olefins 221 is provided to an apparatus 230 configured to separate the mixture of $C_4$ olefins 221 into a stream including the $C_4$ olefins 231 and a stream including the $C_{5+}$ olefins 282.

The stream including $C_4$ olefins 231 is then treated with an apparatus 240 configured to remove any $C_4$ alcohols. The resulting stream of $C_4$ olefins 241 is then provided to a metathesis reactor 250. A butenes purge 281 from apparatus 240 may be collected and recycled. The butenes 281 may be combined with the feed of isobutylene, combined with the stream of $C_4$ olefins 241, provided directly to apparatus 250 (not shown), or a combination thereof.

In the metathesis reactor 250, the stream of $C_4$ olefins 241 is contacted with a metathesis catalyst, optionally in the presence of an isomerization catalyst, to produce a product mixture 251 that may include ethylene, propylene, unreacted isobutylene, butene-1, cis-butene-2, trans-butene-2, and $C_{5+}$ olefins.

The product mixture then is provided to an apparatus 260 configured to separate a stream including ethylene 261 from the ethylene-free product mixture 262.

The ethylene-free product mixture 262 then is provided to an apparatus 270 configured to separate a stream including propylene 271 from the ethylene- and propylene-free product mixture 272.

The ethylene- and propylene-free product mixture 272 then is provided to the apparatus 230 to separate a stream including butenes 231 from a stream including $C_{5+}$ olefins 282. The method schematically depicted at FIG. 2 may be aided by one or more other components known to those of ordinary skill in the art, such as one or more valves, furnaces, compressors, pumps, etc.

Figure 3:
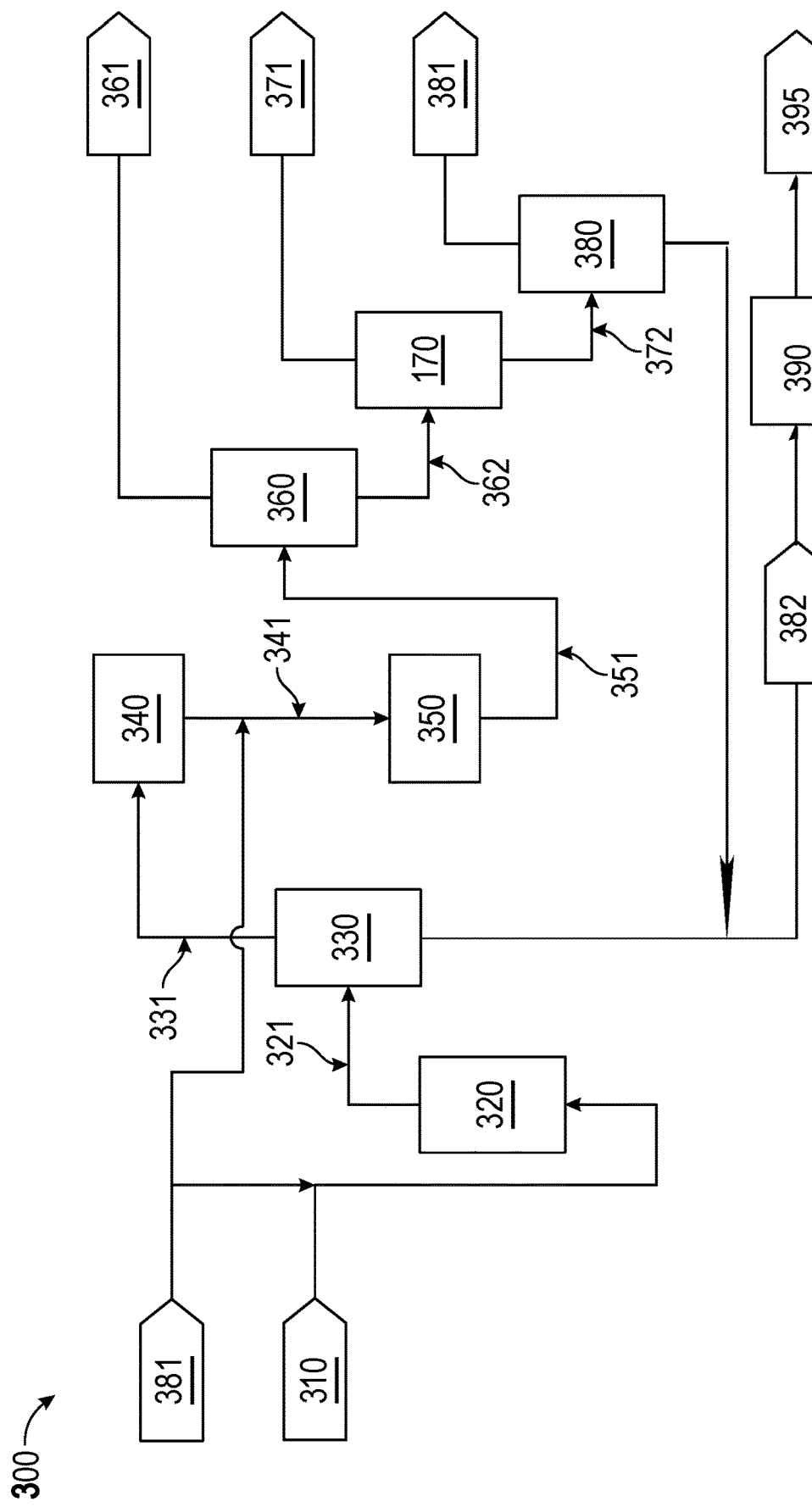
FIG. 3 depicts a schematic of an embodiment of a method described herein.

A schematic of an embodiment of a method described herein is depicted at FIG. 3. The method 300 of FIG. 3 includes a feed of isobutylene 310 that is provided to an isomerization reactor 320. The isobutylene 310 is contacted with a skeletal isomerization catalyst in the isomerization reactor 320 to produce a mixture of $C_4$ olefins 321. The mixture of $C_4$ olefins 321 may also include ethylene, propylene, and $C_{5+}$ olefins.

Thereafter, the mixture of $C_4$ olefins 321 is provided to an apparatus 330 configured to separate the mixture of $C_4$ olefins 321 into a stream including the $C_4$ olefins 331 and a stream including the $C_{5+}$ olefins 382.

The stream including $C_4$ olefins 331 is then treated with an apparatus 340 configured to remove any $C_4$ alcohols. The resulting stream of $C_4$ olefins 341 is then provided to a metathesis reactor 350. In the metathesis reactor 350, the stream of $C_4$ olefins 341 is contacted with a metathesis catalyst, optionally in the presence of an isomerization catalyst, to produce a product mixture 351 that may include ethylene, propylene, unreacted isobutylene, butene-1, cis-butene-2, trans-butene-2, and $C_{5+}$ olefins.

The product mixture then is provided to an apparatus 360 configured to separate a stream including ethylene 361 from the ethylene-free product mixture 362.

The ethylene-free product mixture 362 then is provided to an apparatus 370 configured to separate a stream including propylene 371 from the ethylene- and propylene-free product mixture 372.

The ethylene- and propylene-free product mixture 372 then is provided to an apparatus 380 configured to separate a stream including butenes 381 from a stream including $C_{5+}$ olefins 382. The stream including butenes 381 may optionally be recycled, as depicted at FIG. 3. The stream including butenes 381 may be combined with the feed of isobutylene, combined with the stream of $C_4$ olefins 341, provided directly to apparatus 350 (not shown), or a combination thereof.

The stream of $C_{5+}$ olefins of apparatus 330 and apparatus 380 may be combined as depicted at FIG. 3, or the streams may be handled or treated separately. The stream of $C_{5+}$ olefins 382 may be directed to hydrotreating unit 390 to produce treated product stream 395. The method schematically depicted at FIG. 3 may be aided by one or more other components known to those of ordinary skill in the art, such as one or more valves, furnaces, compressors, pumps, etc.

Figure 4:
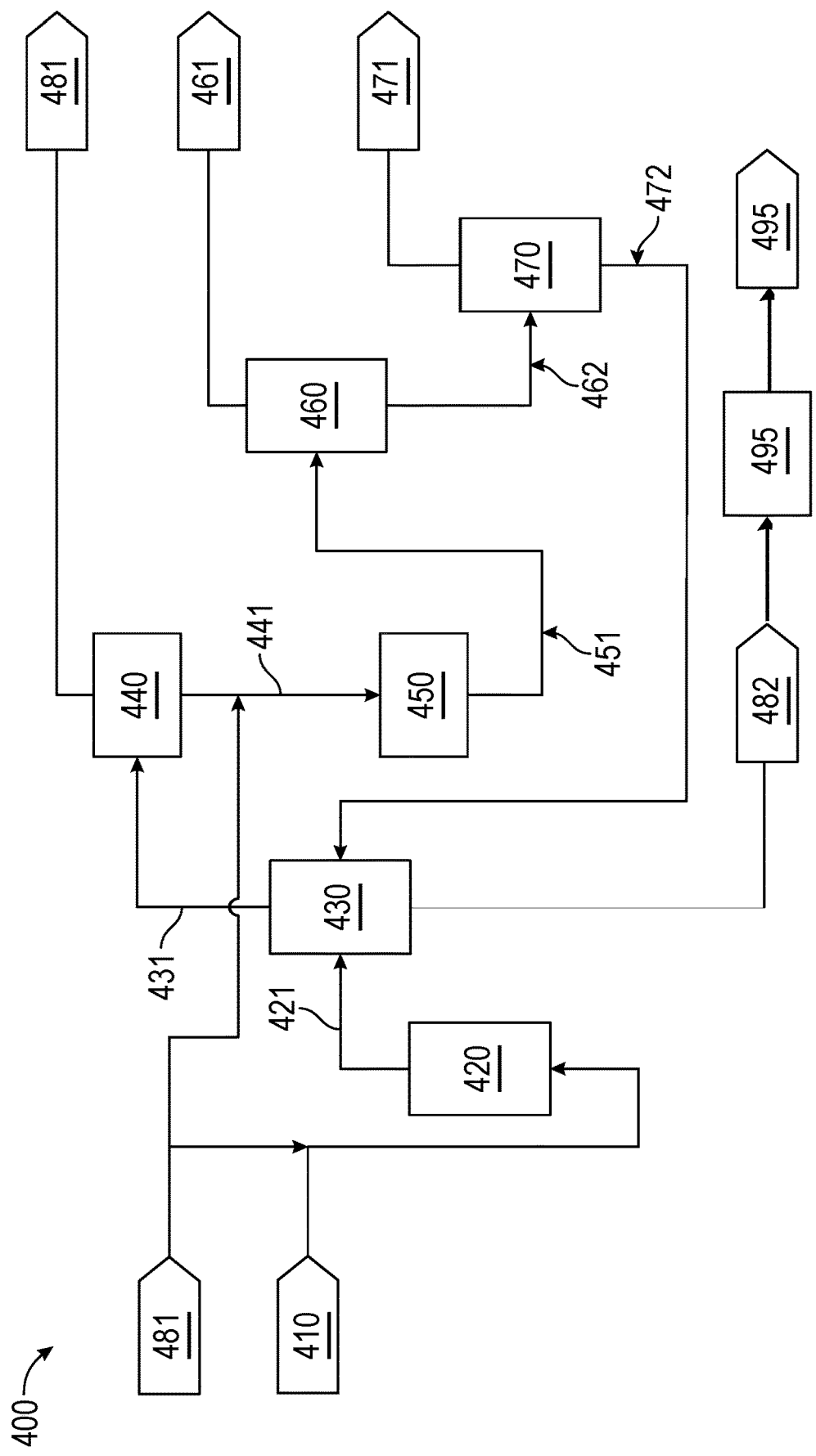
FIG. 4 depicts a schematic of an embodiment of a method described herein.

A schematic of an embodiment of a method described herein is depicted at FIG. 4. The method 400 of FIG. 4 includes a feed of isobutylene 410 that is provided to an isomerization reactor 420. The isobutylene 410 is contacted with a skeletal isomerization catalyst in the isomerization reactor 420 to produce a mixture of $C_4$ olefins 421. The mixture of $C_4$ olefins 421 may also include ethylene, propylene, and $C_{5+}$ olefins.

Therefore, the mixture of $C_4$ olefins 421 is provided to an apparatus 430 configured to separate the mixture of $C_4$ olefins 421 into a stream including the $C_4$ olefins 431 and a stream including the $C_{5+}$ olefins 482.

The stream including $C_4$ olefins 431 is then treated with an apparatus 440 configured to remove any $C_4$ alcohols. The resulting stream of $C_4$ olefins 441 is then provided to a metathesis reactor 450. A butenes purge 481 from apparatus 440 may be collected and recycled. The butenes 481 may be combined with the feed of isobutylene, combined with the stream of $C_4$ olefins 441, provided directly to apparatus 450 (not shown), or a combination thereof.

In the metathesis reactor 450, the stream of $C_4$ olefins 441 is contacted with a metathesis catalyst, optionally in the presence of an isomerization catalyst, to produce a product mixture 451 that may include ethylene, propylene, unreacted isobutylene, butene-1, cis-butene-2, trans-butene-2, and $C_{5+}$ olefins.

The product mixture then is provided to an apparatus 460 configured to separate a stream including ethylene 461 from the ethylene-free product mixture 462.

The ethylene-free product mixture 462 then is provided to an apparatus 470 configured to separate a stream including propylene 471 from the ethylene- and propylene-free product mixture 472.

The ethylene- and propylene-free product mixture 472 then is provided to the apparatus 430 to separate a stream including butenes 431 from a stream including $C_{5+}$ olefins 482. The stream of $C_{5+}$ olefins 482 may be directed to hydrotreating unit 490 to produce treated product stream 495. The method schematically depicted at FIG. 4 may be aided by one or more other components known to those of ordinary skill in the art, such as one or more valves, furnaces, compressors, pumps, etc.

In the descriptions provided herein, the terms "includes," "is," "containing," "having," and "comprises" are used in an open-ended fashion, and thus should be interpreted to mean "including, but not limited to." When methods or compositions are claimed or described in terms of "comprising" or "including" various elements or features, the methods can also "consist essentially of" or "consist of" the various components or features, unless stated otherwise.

The terms "a," "an," and "the" are intended to include plural alternatives, e.g., at least one. For instance, the disclosure of "a product mixture," "a zeolitic catalyst," "a debutenizer", and the like, is meant to encompass one, or mixtures or combinations of more than one product mixture, zeolitic catalyst, debutenizer, and the like, unless otherwise specified.

Various numerical ranges may be disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. Moreover, numerical end points of ranges disclosed herein are approximate. As a representative example, Applicant discloses that, in some embodiments, at thermodynamic equilibrium the butene-1 is present in the mixture of $C_4$ olefins at an amount of about 10% to about 15%, by weight, based on the weight of the $C_4$ olefins. This disclosure should be interpreted as encompassing values of about 10% and 15%, and further encompasses "about" each of 11%, 12%, 13%, and 14%, including any ranges and sub-ranges between any of these values.

The present embodiments are illustrated herein by referring to various embodiments, which are not to be construed in any way as imposing limitations upon the scope thereof. On the contrary, it is to be understood that resort may be had to various other aspects, embodiments, modifications, and equivalents thereof which, after reading the description herein, may suggest themselves to one of ordinary skill in the art without departing from the spirit of the present embodiments or the scope of the appended claims. Thus, other aspects of the embodiments will be apparent to those skilled in the art from consideration of the specification and practice of the embodiments disclosed herein.

As used herein, the term "about" refers to values within ±5% or ±1% of the numerical value associated with the term.

The present disclosure is further illustrated by the following examples, which are not to be construed in any way as imposing limitations upon the scope thereof. On the contrary, it is to be understood that resort may be had to various other aspects, embodiments, modifications, and equivalents thereof which, after reading the description herein, may suggest themselves to one of ordinary skill in the art without departing from the spirit of the present disclosure or the scope of the appended claims. Thus, other aspects of this disclosure will be apparent to those skilled in the art from consideration of the specification and practice of the disclosure disclosed herein.

EXAMPLES

Example 1—Isobutylene Conversion

In this example, fresh isobutylene was fed to a first reactor, where the isobutylene underwent skeletal isomerization to a mixture of $C_4$ olefins. The $C_4$ olefins of this example included butene-1 (B1), cis-butene-2 (B2), trans-butene-2 (B2), and unconverted isobutylene, along with minor side products, such as ethylene, propylene, and $C_{5+}$ olefins.

The effluent distribution reached a thermodynamic equilibrium with an active zeolitic catalyst. In this example, the following product distribution was achieved at a reaction temperature of about 750° F. (i.e., about 399° C.).

TABLE 1

| Product Distribution at Thermodynamic Equilibrium at 750° F. | | | | |
|---|---|---|---|---|
| Product | Isobutylene | B1 | B2 | C2, 3 and C5+ Olefin |
| Weight % | 42 | 12 | 36 | 10 |

The lighter products—i.e., ethylene ($C_2$) and propylene ($C_3$)—and product heavies—i.e., $C_{5+}$ olefins—were then removed from the mixture of $C_4$ olefins.

The mixture of $C_4$ olefins was then further processed in a second reactor. The further processing resulted in more gasoline components, as well as propylene.

In some tests of this example, some light olefins—i.e., $C_2$ and $C_3$ olefins—were recycled in order to increase or maximize gasoline selectivity.

Autometathesis of the mixture of $C_4$ olefins was then conducted. The butene autometathesis of this example reached a thermodynamic equilibrium at 392° F. (i.e., 200° C.) with a Group VIB active catalyst. In some tests, the Group VIB active catalyst was used in the presence of an isomerization catalyst.

The following table provides the product distribution observed after the mixture of $C_4$ olefins was processed in the metathesis reactor. The unconverted butenes were recycled to the metathesis reactor to completion.

TABLE 2

| Product Distribution at Thermodynamic Equilibrium of Butene Autometathesis at 392° F. | | | | | | | | |
|---|---|---|---|---|---|---|---|---|
| Product | C2 | C3 | IB | B1 | B2 | C5+ | IB Conv. | $C_4$ Conv. |
| Weight % | 2 | 19 | 23 | 3 | 18 | 35 | 51 | 57 |

The product distribution of Table 2 may differ if the process were modified in order achieve a desired product optimization, energy efficiency, capital cost reduction, or a combination thereof.

ADDITIONAL DISCLOSURE

Embodiments disclosed herein include:

A: a method of converting isobutylene, the method comprising: (a) contacting isobutylene and a skeletal isomerization catalyst to convert the isobutylene to a mixture of $C_4$ olefins, wherein the mixture of $C_4$ olefins comprises butene-1, cis-butene-2, trans-butene-2, unreacted isobutylene, or a combination thereof; (b) contacting the mixture of $C_4$ olefins with a metathesis catalyst to convert the mixture of $C_4$ olefins to a product mixture, wherein the product mixture comprises ethylene, propylene, unreacted isobutylene, butene-1, cis-butene-2, trans-butene-2, and $C_{5+}$ olefins, and the $C_{5+}$ olefins are present in the product mixture at an amount of at least 25%, by weight, based on the weight of the product mixture.

Embodiment A may have one or more of the following additional elements:

Element 1: wherein the $C_{5+}$ olefins are present in the product mixture at an amount of at least 27%, by weight, based on the weight of the product mixture. Element 2: wherein the $C_{5+}$ olefins are present in the product mixture at an amount of at least 29%, by weight, based on the weight of the product mixture. Element 3: wherein the $C_{5+}$ olefins are present in the product mixture at an amount of at least 31%, by weight, based on the weight of the product mixture. Element 4: wherein the $C_{5+}$ olefins are present in the product mixture at an amount of at least 33%, by weight, based on the weight of the product mixture. Element 5: wherein the $C_{5+}$ olefins are present in the product mixture at an amount of at least 35%, by weight, based on the weight of the product mixture. Element 6: further comprising separating the $C_{5+}$ olefins from the product mixture. Element 7: further comprising (i) blending the $C_{5+}$ olefins with one or more other components to produce a product, (ii) processing the $C_{5+}$ olefins in a hydrotreater, or (iii) a combination thereof. Element 8: wherein the product comprises gasoline. Element 9: wherein at thermodynamic equilibrium the butene-1 is present in the mixture of $C_4$ olefins at an amount of about 5% to about 20%, by weight, based on the weight of the $C_4$ olefins. Element 10: wherein at thermodynamic equilibrium the butene-1 is present in the mixture of $C_4$ olefins at an amount of about 10% to about 15%, by weight, based on the weight of the $C_4$ olefins. Element 11: wherein at thermodynamic equilibrium the cis-butene-2 and the trans-butene-2 are present in the mixture of $C_4$ olefins at a total amount of about 25% to about 45%, by weight, based on the weight of the $C_4$ olefins. Element 12: wherein at thermodynamic equilibrium the cis-butene-2 and the trans-butene-2 are present in the mixture of $C_4$ olefins at a total amount of about 30% to about 40%, by weight, based on the weight of the $C_4$ olefins. Element 13: wherein at thermodynamic equilibrium the mixture of $C_4$ olefins further comprises ethylene, propylene, $C_{5+}$ olefins, or a combination thereof, wherein the ethylene, propylene, $C_{5+}$ olefins, or a combination thereof are present in the mixture of $C_4$ olefins at a total amount of 0% to about 15%, by weight, based on the weight of the mixture of $C_4$ olefins. Element 14: further comprising separating the ethylene, the propylene, the $C_{5+}$ olefins, or the combination thereof from the mixture of $C_4$ olefins prior to the contacting of the mixture of $C_4$ olefins with the metathesis catalyst. Element 15: further comprising separating the $C_{5+}$ olefins from the mixture of $C_4$ olefins prior to the contacting of the mixture of $C_4$ olefins with the metathesis catalyst. Element 16: further comprising (i) blending the $C_{5+}$ olefins with one or more other components to produce a product, (ii) processing the $C_{5+}$ olefins in a hydrotreater, or (iii) a combination thereof. Element 17: wherein the skeletal isomerization catalyst comprises a zeolitic catalyst. Element 18: further comprising separating the ethylene from the product mixture to create a substantially ethylene-free product mixture. Element 19: further comprising separating the propylene from the substantially ethylene-free product mixture to produce a substantially ethylene- and propylene-free product mixture. Element 20: further comprising separating the unreacted isobutylene, the butene-1, the cis-butene-2, and the trans-butene-2 from the substantially ethylene- and propylene-free product mixture to produce a substantially ethylene-, propylene-, and butene-free product mixture comprising the $C_{5+}$ olefins. Element 21: wherein an amount of the unreacted isobutylene that is present in the mixture of $C_4$ olefins is about 1.5 times to about 2.5 times greater than an amount of the unreacted isobutylene that is present in the product mixture. Element 22: wherein an amount of the unreacted isobutylene that is present in the mixture of $C_4$ olefins is about 2 times greater than an amount of the unreacted isobutylene that is present in the product mixture.

The particular embodiments disclosed above are merely illustrative, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and such variations are considered within the scope and spirit of the present disclosure. Alternative embodiments that result from combining, integrating, and/or omitting features of the embodiment(s) are also within the scope of the disclosure.

Accordingly, the scope of protection is not limited by the description set out above but is only limited by the claims which follow, such scope including equivalents of the subject matter of the claims.

What is claimed is:

1. A method of converting isobutylene, the method comprising:
    contacting isobutylene and a skeletal isomerization catalyst to convert the isobutylene to a mixture of $C_4$ olefins, wherein the mixture of $C_4$ olefins comprises butene-1, cis-butene-2, trans-butene-2, unreacted isobutylene, or a combination thereof;
    contacting the mixture of $C_4$ olefins with a metathesis catalyst to convert the mixture of $C_4$ olefins to a product mixture,
    wherein the product mixture comprises ethylene, propylene, unreacted isobutylene, butene-1, cis-butene-2, trans-butene-2, and $C_{5+}$ olefins, and the $C_{5+}$ olefins are present in the product mixture at an amount of at least 25%, by weight, based on the weight of the product mixture.

2. The method of claim 1, wherein the $C_{5+}$ olefins are present in the product mixture at an amount of at least 35%, by weight, based on the weight of the product mixture.

3. The method of claim 1, further comprising separating the $C_{5+}$ olefins from the product mixture.

4. The method of claim 3, further comprising (i) blending the $C_{5+}$ olefins with one or more other components to produce a product, (ii) processing the $C_{5+}$ olefins in a hydrotreater, or (iii) a combination thereof.

5. The method of claim 4, wherein the product comprises gasoline.

6. The method of claim 1, wherein at thermodynamic equilibrium the butene-1 is present in the mixture of $C_4$ olefins at an amount of about 5% to about 20%, by weight, based on the weight of the $C_4$ olefins.

7. The method of claim 1, wherein at thermodynamic equilibrium the butene-1 is present in the mixture of $C_4$ olefins at an amount of about 10% to about 15%, by weight, based on the weight of the $C_4$ olefins.

8. The method of claim 1, wherein at thermodynamic equilibrium the cis-butene-2 and the trans-butene-2 are present in the mixture of $C_4$ olefins at a total amount of about 25% to about 45%, by weight, based on the weight of the $C_4$ olefins.

9. The method of claim 1, wherein at thermodynamic equilibrium the cis-butene-2 and the trans-butene-2 are present in the mixture of $C_4$ olefins at a total amount of about 30% to about 40%, by weight, based on the weight of the $C_4$ olefins.

10. The method of claim 1, wherein at thermodynamic equilibrium the mixture of $C_4$ olefins further comprises ethylene, propylene, $C_{5+}$ olefins, or a combination thereof, wherein the ethylene, propylene, $C_{5+}$ olefins, or a combination thereof are present in the mixture of $C_4$ olefins at a total amount of 0% to about 15%, by weight, based on the weight of the mixture of $C_4$ olefins.

11. The method of claim 10, further comprising separating the ethylene, the propylene, the $C_{5+}$ olefins, or the combination thereof from the mixture of $C_4$ olefins prior to the contacting of the mixture of $C_4$ olefins with the metathesis catalyst.

12. The method of claim 10, further comprising separating the $C_{5+}$ olefins from the mixture of $C_4$ olefins prior to the contacting of the mixture of $C_4$ olefins with the metathesis catalyst.

13. The method of claim 12, further comprising (i) blending the $C_{5+}$ olefins with one or more other components to produce a product, (ii) processing the $C_{5+}$ olefins in a hydrotreater, or (iii) a combination thereof.

14. The method of claim 1, wherein the skeletal isomerization catalyst comprises a zeolitic catalyst.

15. The method of claim 1, further comprising separating the ethylene from the product mixture to create a substantially ethylene-free product mixture.

16. The method of claim 15, further comprising separating the propylene from the substantially ethylene-free product mixture to produce a substantially ethylene- and propylene-free product mixture.

17. The method of claim 16, further comprising separating the unreacted isobutylene, the butene-1, the cis-butene-2, and the trans-butene-2 from the substantially ethylene- and propylene-free product mixture to produce a substantially ethylene-, propylene-, and butene-free product mixture comprising the $C_{5+}$ olefins.

18. The method of claim 1, wherein an amount of the unreacted isobutylene that is present in the mixture of $C_4$ olefins is about 1.5 times to about 2.5 times greater than an amount of the unreacted isobutylene that is present in the product mixture.

19. The method of claim 1, wherein an amount of the unreacted isobutylene that is present in the mixture of $C_4$ olefins is about 2 times greater than an amount of the unreacted isobutylene that is present in the product mixture.

* * * * *